(12) United States Patent
Yang et al.

(10) Patent No.: US 11,351,215 B2
(45) Date of Patent: Jun. 7, 2022

(54) COMPOSITION FOR PREVENTING HAIR LOSS AND STIMULATING HAIR-GROWTH

(71) Applicant: MOTHER"S PHARMACEUTICAL CO., LTD., Seoul (KR)

(72) Inventors: Min Kyu Yang, Gyeonggi-do (KR); Jwa Jin Kim, Seoul (KR)

(73) Assignee: MOTHER"S PHARMACEUTICAL CO., LTD., Seoul (KR)

( * ) Notice: Subject to any disclaimer, the term of this patent is extended or adjusted under 35 U.S.C. 154(b) by 0 days.

(21) Appl. No.: 16/976,061

(22) PCT Filed: Feb. 27, 2019

(86) PCT No.: PCT/KR2019/002378
§ 371 (c)(1),
(2) Date: Aug. 26, 2020

(87) PCT Pub. No.: WO2019/168348
PCT Pub. Date: Sep. 6, 2019

(65) Prior Publication Data
US 2021/0138011 A1 May 13, 2021

(30) Foreign Application Priority Data
Feb. 28, 2018 (KR) .................. 10-2018-0024228

(51) Int. Cl.
*A61K 36/28* (2006.01)
*A61P 17/14* (2006.01)
*A61K 9/00* (2006.01)
*A61K 47/10* (2017.01)

(52) U.S. Cl.
CPC ............ *A61K 36/28* (2013.01); *A61K 9/0014* (2013.01); *A61K 47/10* (2013.01); *A61P 17/14* (2018.01); *A61K 2236/333* (2013.01); *A61K 2236/39* (2013.01)

(58) Field of Classification Search
None
See application file for complete search history.

(56) References Cited

U.S. PATENT DOCUMENTS

| 3,382,247 A | 5/1968 | Anthony et al. |
| 5,215,894 A | 6/1993 | Arison et al. |
| 5,804,206 A | 9/1998 | D'Amelio et al. |
| 9,737,469 B2 | 8/2017 | Christiano et al. |
| 2007/0190075 A1 | 8/2007 | Suzuki et al. |

FOREIGN PATENT DOCUMENTS

| CN | 102824292 A | 12/2012 |
| JP | 2000344653 A | 12/2000 |
| JP | 2013136551 | 7/2013 |
| KR | 1020130042944 A | 4/2013 |
| KR | 20170055172 A | 5/2017 |
| KR | 1020170055172 A | 5/2017 |
| KR | 1017976670000 B1 | 12/2017 |

OTHER PUBLICATIONS

Raskin et al. (2004) Current Pharmaceutical Design, 10: 3419-3429. (Year: 2004).*
Revilla et al. (1998) J. Agric. Food Chem. 46: 4592-4597. (Year: 1998).*
Chinese Office Action dated Oct. 27, 2021, Chinese Patent Application No. 201980015927.3, 6 pages.
Extended European Search Report dated Oct. 19, 2021, European Appl. No. 19761640.2, 6 pages.
Soetardjo et al., "Chemical Composition and Biological Activity of the *Centipeda minima* (Asteraceae)" Mal J. Nutr 2007, 13(1): 81-87.
Thomson Scientific, London, GB; AN 2017-347818.
Ramezanpour, M., et al., 'The Relationship Between Janus Kinase Pathways and MicroRNAs,' Trends in Peptide and Protein Sciences, vol. 1, No. 4, p. 144-152, Jul. 10, 2017.
Chan, C., et al., 'Qualitative and quantitative analysis of chemical constituents of Centipeda minima by HPLCQTOF-MS & HPLC-DAD,' Journal of Pharmaceutical and Biomedical Analysis vol. 125, p. 400-407, Jun. 5, 2016.
Wu, J-B, et al., Biologically Active constituents of Centipeda minima: Sesquiterpenes erf Potential Anti-Allergy Activity, Chem. Pharm. Bull. 39(12) p. 3272-3275, Jun. 24, 1991.
Japan Patent Office, First Office Action for Japanese Application: JP 2020568652, dated Mar. 9, 2022.

* cited by examiner

*Primary Examiner* — Russell G Fiebig
(74) *Attorney, Agent, or Firm* — Casimir Jones S.C.; Lisa Mueller

(57) ABSTRACT

The present disclosure relates to a composition including a *Centipeda minima* extract and the fraction thereof as an active ingredient. Since the composition of the present disclosure promotes the production and growth of hair, the composition not only presents excellent effects in the prevention, amelioration, and treatment of hair-loss, but may also be used for promoting hair-growth.

5 Claims, 11 Drawing Sheets

Fig. 1

| | Test substance-administered group | Positive control group 1 | Positive control group 2 |
|---|---|---|---|
| Day 1 | | | |
| Day 2 | | | |
| Day 3 | | | |
| Day 4 | | | |
| Day 5 | | | |
| Day 6 | | | |
| Day 7 | | | |

(A)

(B)

(A)

(B)

COMPOSITION FOR PREVENTING HAIR LOSS AND STIMULATING HAIR-GROWTH

CROSS-REFERENCE TO RELATED APPLICATIONS

This application is a national phase application under 35 U.S.C. § 371 of PCT International Application No. PCT/KR2019/002378, filed Feb. 27, 2019, which claims the benefit of Korean Application No. 10-2018-0024228, filed Feb. 28, 2018, each of which are herein incorporated by reference.

TECHNICAL FIELD

The present disclosure relates to a composition for preventing, ameliorating or treating hair-loss, a composition for stimulating hair-growth, and uses thereof.

BACKGROUND ART

Hair-loss is one of diseases with a high prevalence due to congenital factors (genetic factors) and acquired factors (environment, eating habits, autoimmune diseases). There are more than 140 million hair-loss populations worldwide. That is, 14% of the world's population are hair-loss patients. Domestic hair-loss population has increased annually to reach 10 million people. In particular, a percentage of hair-loss patients in their 20s and 30s which are the most sensitive to looks thereof is 48.5%. Thus, 20s and 30s are the largest hair-loss groups among all age groups.

Hair-loss develops due to irregular lifestyle and stress, male hormones, aging, genetic and nutritional imbalances. Due to hair softening phenomenon, hair becomes thin and weak and anagen is shortened. Thus, hair is removed in telogen or catagen. A hair follicle is not supplied with nutrients due to shrinkage of the hair follicle, resulting in loss of a function of the hair follicle and eventually hair-loss.

Treatment approaches for the hair-loss have no clear effect yet. In Donguibogam, there are some prescriptions that are related to hair-loss, such as sin-eung-yang-jin-dan (新應養眞丹), massaging the hair-loss area with homayu (胡麻油) (sesame oil), applying a specific herbal medicine prescription on the hair-loss area, and stimulating a specific acupuncture point. However, there are differences in effects thereof between individuals.

As a conventional treatment method for the hair-loss, there are preparations based on female hormones in connection with a hormonal theory. However, there are reports of skin inflammation, side effects caused by the hormone administration, etc., and thus the use thereof is currently discontinued. Representative hair-growth agents that have recently been used were first developed and used them for promoting blood circulation but had a hair-growth effect as a side effect thereof, and thus were approved as a hair-growth composition by the U.S. Food and Drug Administration (FDA). Those agents are minoxidil (6-amino-1,2-dihydro-1-hydroxy-2-imino-4-phenoxypyrimidine) as disclosed in U.S. Pat. No. 3,382,247, and finasteride from the Merck company as disclosed in U.S. Pat. No. 5,215,894.

In this connection, the minoxidil and finasteride are widely used for the hair-loss treatments based on 5-alpha-reductase inhibitors, but have side effects such as depression, sexual dysfunction and the like, and must be taken for a long time. Reports have been published that when the minoxidil and finasteride-based treatment is discontinued, the hair-loss begins again, and the toxicity is found therein.

As such, the hair-loss treatment agent on the current market may be ineffective or should be taken for a long time, and may have the toxicity and the side effects. Thus, patients seeking surgical procedures in order to treat the hair-loss are increasing year by year.

Therefore, recently, studies on the hair-loss treatment substances that have been extracted and separated from natural plants and have little toxicity and minimize side effects during long-term use are being actively conducted.

In this connection, *Centipeda minima* is a yearly plant of the genus Phanerophytes, Magnoliopsida, *Chrysanthemum, Chrysanthemum Centipeda minima*, and is distributed in Korea, Japan, China, India, Australia, eastern Siberia. North America, and the like. In a folk medicine in China. *Centipeda minima* has efficacy against rhinitis, sinusitis, and of pain relief, swelling reduction, anti-cancer, liver protection, nerve protection, etc. Further, it is known that it is effective for chronic malaria by rubbing leaves and stems thereof and inserting the same into the nostrils and staying overnight in this state. *Centipeda minima* is also used in India for eye disease, nose disease, and toothache. However, there is no known hair-growth effect or hair-loss prevention and hair-growth-related efficacy thereof.

Korea Patent No. 10-1810139
Korea Patent No. 10-1797667
U.S. Pat. No. 5,215,894

DISCLOSURE

Technical Problem

A purpose of the present disclosure is to provide a pharmaceutical composition for the prevention or treatment of hair-loss.

Another purpose of the present disclosure is to provide a food composition for preventing or ameliorating hair-loss.

Another purpose of the present disclosure is to provide a cosmetic composition for preventing or ameliorating hair-loss.

Another purpose of the present disclosure is to provide a quasi-drug composition for preventing or ameliorating hair-loss.

Another purpose of the present disclosure is to provide a composition for stimulating hair-growth.

Another purpose of the present disclosure is to provide a method for treating hair-loss.

Another purpose of the present disclosure is to provide various uses of *Centipeda minima* extract and/the fraction thereof for treatment of hair-loss.

Technical Solution

To achieve the purposes, the present inventors continued to study new substances that could replace the existing hair-loss treatment and hair-growth agents. Thus, we have identified that *Centipeda minima* extract and/the fraction thereof have excellent effects on the prevention, treatment, and amelioration of hair-loss and the effect of stimulating the hair-growth. Thus, the present disclosure was completed.

Hair follicles in telogen or catagen may enter anagen due to administration of the composition according to the present disclosure. The main feature of the hair follicle in the anagen is a hair bulb located at the bottom of the hair follicle. The hair bulb is located at the lower part of a subcutaneous fat layer. In the anagen, the hair follicle has the longest length and is surrounded by highly proliferative, undifferentiated cells. When the number of hair follicles in anagen increases, the skin turns black and the skin becomes the thickest. The anagen of the hair follicle may start from the beginning of development and may last for, for example, approximately two weeks.

The present disclosure provides a pharmaceutical composition for the prevention or treatment of hair-loss, the composition containing a *Centipeda minima* extract or fractions thereof.

In the present disclosure, there are no restrictions on how to obtain *Centipeda minima*. *Centipeda minima* may be cultivated or commercially available. In the present disclosure, the *Centipeda minima* may be a living *Centipeda minima*, pulverized product, dried product, dried pulverized product, fermented product, extract and/or fraction thereof. Specifically, in various compositions according to the present disclosure, *Centipeda minima* is a *Centipeda minima* extract or a fraction thereof. In the present disclosure, *Centipeda minima* extract may be extracted from any one or more selected from leaves, petals, roots, stems, fruits of *Centipeda minima* or combinations thereof. For example, *Centipeda minima* extract may be extracted from the whole herb of *Centipeda minima*, or from a portion or an entirety of an aerial part or a root part of the herb. In a specific embodiment according to the present disclosure, *Centipeda minima* may use *Centipeda minima* plant with or without a flower.

In the present disclosure, the extract includes all substances obtained by extracting active ingredients, etc. from natural substances irrespective of the extraction method, extraction solvent, extracted component or extract type. Further, the extract has a broad concept that includes all substances that may be obtained by extracting substances obtained by extracting components of natural substances and processing or treating the obtained substances in other ways. The "processing or treatment" may be, for example, additionally fermenting or enzymatically treating the extract.

Therefore, in the present application, the extract may include not only the extract, but also a fraction thereof. Further, the extract may include extracts in all formulations formable from *Centipeda minima*, such as a refined or purified product, or a diluent, concentrate, dried product, fermented product of the extract or the fraction thereof or a mixture thereof.

In the present disclosure, the extracts may be prepared using general preparation methods known in the art. The method is not particularly limited. For example, the extract may be prepared by a known method including ultrasonic extraction, supercritical extraction, decompression extraction, reflux extraction, hot water extraction, hot pressurization extraction, ultrahigh pressure extraction, enzyme extraction, solvent extraction, cold extraction, a steam distillation method, an elution method, a compression method, a heat extraction method, a Soxhlet's extraction method, or an extraction solvent-based method. The present disclosure is not limited thereto.

In the present disclosure, the extract may be prepared using water, an organic solvent or a mixture thereof as an extraction solvent. The water may be, for example, but not limited to, distilled water, purified water, sterile water. The organic solvent may be, for example, but not limited to, alcohol, glycerin, butylene glycol, propylene glycol, methyl acetate, ethyl acetate, acetone, benzene, hexane, diethyl ether and dichloromethane.

In the present disclosure, the extract may be extracted using a solvent selected from the group consisting of preferably water, alcohol having 1 to 6 carbon atoms, acetone, ether, benzene, chloroform, ethyl acetate, methylene chloride, hexane, cyclohexane and mixtures thereof as an extraction solvent. The alcohol having 1 to 6 carbon atoms may be preferably an alcohol having 1 to 4 carbon atoms. Preferably, the solvent may be water, an alcohol having 1 to 4 carbon atoms, or a mixed solvent thereof. For example, the solvent may be methanol, ethanol, propanol, isopropanol, butanol, isobutanol, and the like. The above alcohol having 1 to 6 carbon atoms may be preferably an aqueous alcohol solution and may have, for example, 10% to 90% by weight, 15% to 85% by weight, 20 to 80% by weight, 21 to 75% by weight, 22 to 73% by weight, 23 to 70% by weight, 25 to 65% by weight, 25 to 60% by weight, 25 to 55% by weight, 25 to 50% by weight, 25 to 45% by weight, or 25 to 40% by weight. The solvent may include alcohol such as ethanol or methanol with a lower content, thereby not only to reduce the production cost, but also to minimize the alcohol component as an extraction solvent that may be harmful and irritating depending on the administration target. Thus, the extract may be non-harmfully applied to the human body. Further, along with the above advantages, the extract has a sufficiently good effect on the prevention, treatment, and amelioration of hair-loss.

In a specific embodiment according to the present disclosure. *Centipeda minima* extract may be extracted using methanol as an extraction solvent. In a specific embodiment according to the present disclosure, *Centipeda minima* extract may be extracted using an aqueous solution of about 30% by weight methanol as an extraction solvent. In a specific embodiment according to the present disclosure, *Centipeda minima* extract may be extracted using an aqueous solution of about 70% by weight methanol as an extraction solvent.

In a specific embodiment according to the present disclosure, *Centipeda minima* extract may be extracted using ethanol as an extraction solvent. In a specific embodiment according to the present disclosure, *Centipeda minima* extract may be extracted using an aqueous solution of about 30% by weight ethanol as an extraction solvent. In a specific embodiment according to the present disclosure, *Centipeda minima* extract may be extracted using an aqueous solution of about 70% by weight ethanol as an extraction solvent.

In the present disclosure, the fraction refers to a result obtained by performing fractionating to separate a specific component or a specific component group from a mixture containing various components. In the present disclosure, the fractions may be prepared by fractionating the extract.

In the present disclosure, a fractionating solvent used for the preparation of the fraction may, for example, but not limited to, water, alcohols having 1 to 4 carbon atoms, hexane (HX), ethyl acetate (EtOAc), chloroform ($CHCl_3$), dichloromethane ($CH_2 Cl_2$) or mixtures thereof. The fractionating solvents may be used alone or in combination of two or more. Depending on the polarity of the solvents, the fractionating solvents may be sequentially used to prepare each fraction of each solvent. In a specific embodiment according to the present disclosure, the fraction of *Centipeda minima* extract may be any one or more selected from the group consisting of hexane fraction, dichloromethane fraction and acetate fraction. Preferably, the fraction thereof may be a dichloromethane fraction.

For example, the dichloromethane fraction according to the present disclosure may be a dichloromethane fraction separated from the methanol extract of *Centipeda minima*. For example, the dichloromethane fraction according to the present disclosure may be a dichloromethane fraction separated from a 30% by weight aqueous methanol solution extract of *Centipeda minima*. For example, the dichloromethane fraction according to the present disclosure may be a dichloromethane fraction separated from a 70% by weight aqueous methanol solution extract of *Centipeda minima*.

For example, the dichloromethane fraction according to the present disclosure may be a dichloromethane fraction separated from ethanol extract of *Centipeda minima*. For example, the dichloromethane fraction according to the present disclosure may be a dichloromethane fraction separated from a 30% by weight aqueous ethanol extract of *Centipeda minima*. For example, the dichloromethane fraction according to the present disclosure may be a dichloromethane fraction separated from a 70% by weight aqueous ethanol extract of *Centipeda minima*.

The fraction according to the present disclosure shows a sufficiently good effect on the prevention, treatment, and amelioration of hair-loss by enhancing the content of the active ingredient through the process of fractionation from the extract.

In the present disclosure, the extract or the fraction thereof may be used in the form of a purified product as a result obtained by further performing an additional purification process thereof.

The purification may use general methods known in the art. For example, but not limited to, various types of chromatography such as silica gel column chromatography, thin layer chromatography, high performance liquid chromatography, etc. may be used as the purification method.

In the present disclosure, the extract or the fraction thereof may be one in which the solvent is removed therefrom by performing a filtration, concentration or drying process, or all of the filtration, concentration and drying process. The filtration may use, for example, filter paper or a vacuum filter. The concentration may be, for example, a reduced pressure concentrator or a rotary evaporator. The drying may be performed, for example, using spray drying or freeze drying. In the present disclosure, the drying may include evaporation drying, spray drying, freeze drying. Specifically, in the freeze drying, the freeze drying may be performed at −50 to −70° C. for 3 to 4 days.

Further, in the present disclosure, the extract or the fraction thereof may be stored in a deep freezer until use. Concentration and freeze drying may completely remove moisture therefrom. The extract from which the moisture is completely removed may be used in powder form or the powder may be dissolved in distilled water or a conventional solvent for use.

In the present disclosure, *Centipeda minima* extract may have a concentration of 0.01 μg/mL to 2,000 μg/mL based on the total volume of the composition, but is not limited thereto.

In the present disclosure, the hair-loss refers to a phenomenon in which hair is removed from the skin or a state in which hair is sparse or thin, and is a term that may be used interchangeably with alopecia.

In the present disclosure, the hair includes hair roots and hair follicles on the head, hairs on the head, eyelashes and eyebrows, beards, armpit hair, pubic hair, and hair roots and hair follicles throughout the body.

In the present disclosure, the hair-loss includes at least one selected from a group consisting of denutrition-based alopecia, endocrine disorder-based alopecia, vascular disorder-based alopecia, alopecia premature, traction alopecia, alopecia areata, alopecia neurotica, pityriasis alopecia, Trichotillomania, alopecia maligna, female pattern alopecia, male pattern alopecia, androgenetic alopecia, telogen effluvium, tinea capitis, alopecia totalis hypotrichosis, genetic hypotrichosis simplex, systemic drug for alopecia-based hair-loss, mechanical hair-loss, traumatic alopecia, pressure alopecia, anagen effluvium, pityriasis alopecia, alopecia syphilltica, lopecia seborrheica, symptomatic alopecia, alopecia cicatrisata, and alopecia congenita. However, the hair-loss should be understood as meaning including all symptoms classified as the alopecia in this field, regardless of the direct or indirect cause of the occurrence of the hair-loss.

According to the present disclosure, a composition including a *Centipeda minima* extract or a fraction thereof may promote hair generation and growth in a state where the hair is removed. According to the present disclosure, a composition containing a *Centipeda minima* extract or a fraction thereof may promote hair generation and growth in a state in which hairs become sparse. According to the present disclosure, a composition containing a *Centipeda minima* extract or a fraction thereof may promote hair generation and growth in a state in which hairs are thinned. According to the present disclosure, a composition containing a *Centipeda minima* extract or a fraction thereof may be intended to maintain hair-growth and prevent hair thinning from the viewpoint of prevention or amelioration of the hair-loss.

In the present disclosure, "active ingredient" refers to a component that may exhibit the desired activity alone, or may exhibit activity with a carrier which is inactive by itself. The active ingredient according to the present disclosure is a *Centipeda minima* extract or a fraction thereof.

In the present disclosure, "prevention" means any action in which the occurrence or development of one or more symptoms associated with hair-loss is suppressed or delayed via administration of a pharmaceutical composition according to the present disclosure, and does not necessarily mean complete suppression of development of the hair-loss.

In the present disclosure, "treatment" refers to any action in which one or more symptoms associated with hair-loss which are being developed or were previously expressed are suppressed, reduced, or ameliorated via administration of a pharmaceutical composition according to the present disclosure to a subject. The subject may be a mammal, including a human. The subject is preferably a human.

In the present disclosure, "administration" means introducing a pharmaceutical composition according to the present disclosure in a subject in any suitable way. The composition may be administered orally or parenterally or any general route as long as the composition reaches a target tissue. Preferably, the composition may be applied to the subject via parenteral administration, more preferably, via topical application. Further, the pharmaceutical composition according to the present disclosure may be administered using any device as long as the device allows the composition to move to a target cell.

The pharmaceutical composition according to the present disclosure may further include a pharmaceutically acceptable carrier in a range that does not impair the effects of the present disclosure. The type of pharmaceutically acceptable carrier that may be used in the present disclosure is not particularly limited. Any carrier commonly used in this technical field may be used. The carrier may include, for example, but not limited to, saline, sterile water, Ringer's solution, buffered saline, albumin injection solution, lactose, dextrose, sucrose, sorbitol, mannitol, xylitol, erythritol, maltitol, maltodextrin, glycerol, ethanol, and the like. The carriers may be used alone or in combination of two or more.

The pharmaceutical composition according to the present disclosure may further include a pharmaceutically acceptable additive in a range that does not impair the effects of the present disclosure. The types of pharmaceutically acceptable additives that may be used in the present disclosure are not particularly limited. Any additives commonly used in the art may be used. The additives may include, for example, but not limited to, fillers, binders, disintegrants, lubricants, suspending agents, solvents, antioxidants, pH adjusting agents, wetting agents, sweeteners and preservatives. The additives may be used alone or in combination of two or more.

The pharmaceutical composition according to the present disclosure may be prepared in suitable and various formulations for oral administration or parenteral administration. In the present disclosure, the formulations for oral administration may include, for example, but not limited to, tablets, pills, powders, powder remedy, granules, pellets, capsules, troches, lozenges, suspensions, emulsions, syrups, elixirs, etc. In the present disclosure, the formulations for parenteral administration may include, for example, but not limited to, injections, suppositories, respiratory inhalers, aerosols, ointments, liquid, lotion, patch, coating powder, oil, cream, gel, etc.

The pharmaceutical composition according to the present disclosure may be administered orally or parenterally depending on the purpose. In the present disclosure, the parenteral administration includes, for example, intraperitoneal administration, rectal administration, subcutaneous administration, intravenous administration, intramuscular administration, thoracic administration, cerebrovascular administration, transdermal administration and hair administration. The composition may be applied to the diseased area sprayed, or inhaled thereon or therein but is not limited thereto. In a specific embodiment according to the present disclosure, the pharmaceutical composition according to the present disclosure may be applied locally.

The pharmaceutical composition according to the present disclosure is administered in a pharmaceutically effective amount. In the present disclosure, "pharmaceutically effective amount" means an amount sufficient to treat a disease at a reasonable benefit/risk ratio applicable to medical treatment. The effective amount levels may be determined based on factors including the patient's condition, weight, gender, age, health status, disease degree, sensitivity to the drug, time of administration, route of administration, rate of discharge, duration of treatment, concurrently used drugs, and other well-known factors in medical fields. The dosage of the pharmaceutical composition according to the present disclosure may be appropriately selected by a person skilled in the art. The dosage of the pharmaceutical composition according to the present disclosure may be a *Centipeda minima* extract of 0.1 mg/kg to 2,000 mg/kg per day. More preferably, the dosage of the pharmaceutical composition according to the present disclosure may be a *Centipeda minima* extract of 1 mg/kg to 500 mg/kg per day, but is not limited thereto. Further, the dosage is not intended to limit the scope of the present disclosure.

The pharmaceutical composition according to the present disclosure may be administered once a day, may be administered several times a day in a divided manner or may be administered once every few days. In a specific embodiment according to the present disclosure, the composition according to the present disclosure may be administered once to 20 times per week, and preferably may be administered twice a day.

The duration of administration of the pharmaceutical composition according to the present disclosure may be determined, by the person skilled in the art, based on factors including the patient's condition, weight, sex, age, health condition, disease degree, sensitivity to the drug, concurrently used drugs, and other well-known factors in medical fields. In a specific embodiment according to the present disclosure, the composition according to the present disclosure may be administered for 1 week to 52 weeks.

The pharmaceutical composition according to the present disclosure may be administered alone or in combination with other prophylactic or therapeutic agents for the prevention and treatment of hair-loss, or may be administered simultaneously or sequentially with other prophylactic or therapeutic agents. Further, the pharmaceutical composition according to the present disclosure may be used in combination with surgery, hormone therapy, chemotherapy and approaches using biological response modifiers.

The present disclosure provides a food composition for preventing or ameliorating hair-loss, the composition containing a *Centipeda minima* extract or a fraction thereof.

In the food composition according to the present disclosure, the *Centipeda minima*, the extract, the fraction and the hair-loss are the same as those described in detail for the pharmaceutical composition according to the present disclosure.

According to a specific example according to the present disclosure, the food composition including the *Centipeda minima* extract or the fraction thereof may be effectively used for preventing or ameliorating the hair-loss.

In the present disclosure, "prevention" means any action in which the occurrence or development of one or more symptoms associated with hair-loss is suppressed or delayed via ingestion of the food composition according to the present disclosure, and does not necessarily mean the complete suppression of development of the hair-loss.

In the present disclosure, "amelioration" means any action in which the degree of one or more symptoms associated with hair-loss is reduced, the symptom is ameliorated or a progress thereof is delayed via the ingestion of the food composition according to the present disclosure.

The food composition according to the present disclosure may have the *Centipeda minima* extract or the fraction thereof as it is. Alternatively, the food composition according to the present disclosure may contain the *Centipeda minima* extract or the fraction thereof together with other food or food ingredients. The food composition may be suitably used according to a conventional method.

The food composition according to the present disclosure contains the *Centipeda minima* extract as an active ingredient. The content of the active ingredient therein may be appropriately determined according to the purpose of use. Generally, the *Centipeda minima* extract may be added in an amount of 0.0001 to 100% by weight based on the total weight of the food composition.

In the present disclosure, there are no particular restrictions on the form of food composition which thus includes all types of foods in the usual sense. The foods to which the present disclosure may be applied may include, for example, beverages, drinks, powders, tablets, and health functional foods.

In the present disclosure, the term "health functional food" refers to a food prepared and processed so that the bio-regulatory function is efficiently expressed in addition to nutrition, using ingredients or components with useful functionality for the human body. The health functional food is sometimes used interchangeably with terms such as a functional food, a health food, or a health supplement food. Further, in the present disclosure, "function" may mean an effect useful for health use via controlling nutrients or physiological action on the structure and function of the human body.

The food composition according to the present disclosure may further include food additives that may generally improve food odor, taste, or vision. The food additives include, for example, but not limited to, flavoring agents, enhancers, and carbonic acid preservatives (potassium sorbate, sodium benzoate, salicylic acid, sodium dihydroacetate, etc.), fungicides (bleaching powder and high-figure bleaching powder, sodium hypochlorite, etc.), antioxidants (butyl hydroxyanisole, butyl hydroxytoluene, etc.), colorants (tar color, etc.), coloring agents (sodium nitrite, sodium acetate, etc.), bleach (sodium sulfite), seasonings (MSG sodium glutamate, etc.), sweeteners (dulcine, cyclamate, saccharin, sodium, etc.), flavoring agents (vanillin, lactones, etc.), swelling agents (alum. D-potassium hydrogen tartrate, etc.), strengthening agents, emulsifiers, thickening agents (paste), coating agents, gum starting agents, antifoaming agents, solvents and improvers. The additives may be selected according to the type of food and used in an appropriate amount.

The food composition according to the present disclosure may further include additional ingredients that may improve the functionality of food. For example, the additional ingredients may include vitamins, niacin, biotin, folate, pantothenic acid, and the like. Further, the additional ingredients may include minerals such as zinc (Zn), iron (Fe), calcium (Ca), chromium (Cr), magnesium (Mg), manganese (Mn), copper (Cu). Further, the additional ingredients may include amino acids such as lysine, tryptophan, cysteine, and valine.

The food composition according to the present disclosure may be used as a food additive or may be added as it is or may be used with other foods or food ingredients, and may be suitably used according to a conventional method.

When the food composition according to the present disclosure is a beverage or drink, the food composition may contain various flavoring agents or natural carbohydrates, etc., as additional ingredients, like a normal beverage. The flavoring agent may include, for example, saccharin, aspartame, and the like. The natural carbohydrates include, for example, conventional sugars such as monosaccharides (glucose, fructose, etc.), disaccharides (maltose, sucrose, etc.), and polysaccharides (dextrin, cyclodextrin, etc.), and sugar alcohols such as xylitol, sorbitol and erythritol. In addition, the food composition according to the present disclosure may contain flesh for the preparation of natural fruit juices, fruit juice drinks and vegetable drinks. These ingredients may be used independently or in combination with each other.

The present disclosure provides a cosmetic composition for preventing or ameliorating the hair-loss, the composition containing a *Centipeda minima* extract or a fraction thereof.

In the cosmetic composition according to the present disclosure, the *Centipeda minima*, extract, fraction, etc. are the same as those described in detail for the pharmaceutical and food compositions according to the present disclosure.

According to a specific example according to the present disclosure, the cosmetic composition containing a *Centipeda minima* extract promotes hair generation and growth, and thus exhibits an excellent effect in preventing or ameliorating hair-loss.

The cosmetic composition according to the present disclosure may be formulated in the form of, for example, but not limited to, solutions, sol gels, suspensions, emulsions, pastes, microcapsules, oils, waxes, aerosols. Specific formulations of the cosmetic composition may include, for example, but not limited to, hair tonic, hair conditioner, hair lotion, hair nutrition lotion, hair shampoo, hair rinse, hair treatment, hair cream, hair nutrition cream, hair moisture cream, hair massage cream, hair wax, hair aerosol, hair pack, hair nutrition pack, hair soap, hair cleansing foam, hair oil, hair drying agent, hair preservation treatment agent, hair dye, hair wave agent, hair bleach, hair gel, hair glaze, hair dressing formulation, hair lacquer, hair moisturizer, hair mousse, hair spray, patch, ointment, waving agents, linement, paste, cataplasma and powder.

The cosmetic composition according to the present disclosure may further include a cosmetically acceptable carrier. The types of the cosmetically acceptable carriers that may be used in the present disclosure are not specifically limited. Any carrier commonly used in the art may be used as the cosmetically acceptable carrier. The carriers may be used alone or in combination of two or more.

The cosmetic composition according to the present disclosure may further include an auxiliary agent commonly used for cosmetic composition in a range that does not impair the effect according to the present disclosure. The type of auxiliary agent that may be used in the present disclosure is not particularly limited. Any auxiliary agent commonly used in this technical field may be used. The auxiliary agent may include, for example, but not limited to, gelling agents, active agents, preservatives, antioxidants, stabilizers, solubilizers, vitamins, solvents, fragrances, fillers, blockers, pigments, odorants and dyes. The auxiliary agents may be used alone or in combination of two or more.

The cosmetic composition according to the present disclosure may be used via a method such as applying or spreading the composition directly on hair or scalp.

The present disclosure provides a quasi-drug composition for the prevention or amelioration of hair-loss, the composition containing a *Centipeda minima* extract or a fraction thereof.

In the quasi-drug composition according to the present disclosure, the *Centipeda minima*, extract, fraction, etc. are the same as those described in detail for the pharmaceutical, food and cosmetic compositions according to the present disclosure.

The quasi-drug composition according to the present disclosure may be effectively used for preventing or ameliorating hair-loss.

In the present disclosure, "quasi-drug" refers to items that are used for the purpose of diagnosing, treating, ameliorating, alleviating, treating or preventing human or animal diseases, and which are less effective than the pharmaceutical products. For example, according to the Pharmaceutical Affairs Law, the quasi-drug is a product other than a product used for the purpose of pharmaceuticals, and used to treat or prevent diseases in humans or animals, and having little or no direct action on the human body.

The quasi-drug composition according to the present disclosure may be prepared in any form that is commonly prepared in the art. For example, but not limited to, the composition may be formulated in the form of a solution, sol gel, suspension, emulsion, paste, microcapsule, oil, wax, and aerosol. Specific formulations of the quasi-drug composition may include, for example, but not limited to, antiseptic cleaners, bath solvents, wet wipes, ointments, creams, lotions, soaps, shampoos, rinses, essences, sprays, patches, and the like.

The quasi-drug composition according to the present disclosure may further include an auxiliary agent commonly used in cosmetic compositions in a range that does not impair the effect of the present disclosure. The type of auxiliary agent that may be used in the present disclosure is not particularly limited. Any auxiliary agent commonly used in this technical field may be used. The auxiliary agent may include, for example, conventional auxiliary agents such as gelling agents, active agents, preservatives, fillers, antioxidants, stabilizers, solubilizers, vitamins, pigments and flavoring agents.

The present disclosure provides a composition for stimulating hair-growth, the composition containing a *Centipeda minima* extract or a fraction thereof.

In the composition for stimulating the hair-growth according to the present disclosure, the *Centipeda minima*, extract, fraction, etc. are the same as those described in detail for the pharmaceutical, food, cosmetic and quasi-drug compositions according to the present disclosure.

In the present disclosure, "hair-growth" refers to the creation and growth of hair, and has a broad concept that includes the meaning of hair-growth or hair-regrowth.

The composition according to the present disclosure may be effectively used for stimulating hair-growth by greatly stimulating hair generation and growth.

The composition for stimulating hair-growth according to the present disclosure may be used as a pharmaceutical, food, cosmetic or quasi-drug composition.

The composition for stimulating hair-growth according to the present disclosure may be administered orally or parenterally depending on the purpose. In the present disclosure, the parenteral administration includes, for example, but not limited to, intraperitoneal administration, rectal administration, subcutaneous administration, intravenous administration, intramuscular administration, chest administration, and transdermal administration. The composition may be applied to the scalp or hair, sprayed, or inhaled thereon or therein. Preferably, the composition may be applied to the scalp or hair or sprayed thereon.

The composition according to the present disclosure may further include an auxiliary component for stimulating hair-growth. The hair-growth-stimulating auxiliary ingredients may include 5-alpha-reductase inhibitory ingredients, hair root and hair follicle cell activating ingredients, hair follicle cell blood flow enhancing ingredients, sterilizing ingredients, anti-dandruff agents, keratin softeners, cooling agents, moisturizers, etc. but not limited thereto.

Further, the present disclosure provides a method for preventing or treating hair-loss, the composition including administering a therapeutically effective amount of the *Centipeda minima* extract or a fraction thereof to a subject in need thereof.

In the present disclosure, the term "therapeutically effective amount (or effective amount)" refers to an appropriate amount that is very sufficient to deliver the desired effect but sufficiently prevent serious side effects within the scope of medical judgment. The administration amount of the *Centipeda minima* extract or the fraction thereof according to the present disclosure into the body may be appropriately adjusted in consideration of the route of administration and the target of administration.

The "administration" means providing the subject with a *Centipeda minima* extract or a fraction thereof according to the disclosure. In this connection, the subject is an animal. Typically, the subject may be a mammal that may have a beneficial effect via treatment with the *Centipeda minima* extract or the fraction thereof according to the present disclosure. Preferred examples of these subjects include primates such as humans.

Moreover, the present disclosure provides a composition including the *Centipeda minima* extract or the fraction thereof for use in the prevention or treatment of hair-loss.

Moreover, the present disclosure provides uses of a composition including the *Centipeda minima* extract or a fraction thereof to produce a drug for the prevention or treatment of hair-loss.

Advantageous Effects

The composition containing the *Centipeda minima* extract or the fraction thereof according to the present disclosure may promote hair generation and growth, and may rapidly transition the telogen hair follicle to the anagen hair follicle. Thus, the effect of stimulating hair-growth and its own health is very excellent. In particular, the *Centipeda minima* is a natural product and has no side effects and toxicity. Tus, it is easy to use the *Centipeda minima* in various administration routes such as application, spraying, and ingestion, and the *Centipeda minima* may be used stably for a long time. Accordingly, the composition according to the present disclosure may be effectively used for preventing, treating or ameliorating the hair-loss, and for stimulating the hair-growth.

DESCRIPTION OF DRAWINGS

FIG. 1 shows a photograph of daily observation of a skin of each of a test substance-administered group, a positive control group 1 and a positive control group 2 in Example 1-1 until 7 days.

MODES OF THE INVENTION

Figure 2:
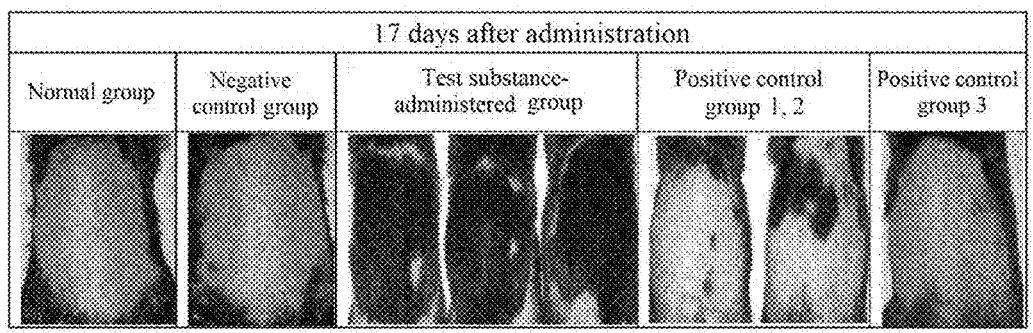
FIG. 2 is a photograph of the normal group, negative control group, test substance-administered group, and positive control groups 1 (1, 2) to 2 (3) after 17 days in Example 1-1.

Hereinafter, the present disclosure will be described in more detail based on specific Preparation Examples and Examples. However, the following Examples are provided only to aid understanding according to the present disclosure, and the scope according to the present disclosure is not limited to Examples.

PREPARATION EXAMPLES

Preparation Example 1: Preparation of *Centipeda minima* Extract

*Centipeda minima* (a dried aerial portion of *Centipeda minima* harvested in Goesan-gun, Chungcheongbuk-do in August 2017) was purchased in September 2017 and used as a sample (Purchased from: Goesan Herbal Organic Agricultural Products Cooperative).

1.0 kg of the purchased *Centipeda minima* was extracted twice (each: 15.0 L×3 days) with 80% methanol (MeOH) at room temperature and then filtered to obtain a *Centipeda minima* extract.

Preparation Examples 2 to 5: Preparation of Fraction of *Centipeda minima* Extract The *Centipeda minima* extract obtained in Preparation Example 1 was evaporated under reduced pressure to obtain 193.2 g of crude extract and then it was suspended in 800 mL distilled water.

The suspension was subjected to systematic solvent fractionation in a sequential direction with increasing polarity using HX (800 mL×3), $CH_2C2$ (800 mL×4), EtOAc (800 mL×3), and n-BuOH (800 mL×3). Each fraction was subjected to concentration under reduced pressure to prepare Preparation Example 2 (HX (23.0 g)) fraction, Preparation Example 3 ($CH_2Cl2$ (9.0 g)) fraction, Preparation Example 4 (EtOAc (9.0 g)) fraction, and Preparation Example 5 (n-BuOH (32.7 g)) fraction.

Preparation Examples 6 to 11: Preparation of *Centipeda minima* Extract

*Centipeda minima* (a dried aerial portion of *Centipeda minima* harvested in Goesan-gun, Chungcheongbuk-do in August 2018) was purchased in September 2018 and used as a sample (Purchased from: Goesan Herbal Organic Agricultural Products Cooperative).

1.0 kg of the purchased *Centipeda minima* was extracted twice (each: 15.0 L 3 days) using each of ethanol (EtOH) 30%, ethanol (EtOH) 70%, ethanol (EtOH) 100%, 30% methanol (MeOH), 70% methanol (MeOH) or 100% methanol (MeOH) at room temperature and then filtered to obtain a *Centipeda minima* extract.

Preparation Examples 12 to 17: Preparation of Fraction of *Centipeda minima* Extract Each extract of Preparation Examples 6 to 11 was subjected to systematic solvent fractionation in a sequential direction in the same manner as the fraction preparation in Preparation Examples 2 to 5. Each fraction was subjected to concentration under reduced pressure to preparea dichloromethane fraction.

PREPARATION EXAMPLE

Preparation Example 1: Preparation of Formulation Containing *Centipeda minima* Extract Tonic formulation-based test substance was prepared using a mixture solvent (65%:5%) of ethanol and glycerin so that the content of *Centipeda minima* extract of Preparation Example 3 was 5% in total.

Preparation Examples 2 to 13: Preparation of Test Substances Containing *Centipeda minima* Extract or Fraction A test substances were prepared using a mixture solvent of 5% Tween 80 and 5% glycerin in distilled water such that a content of each of *Centipeda minima* extracts or Dichloromethane fractions of Preparation Examples 6 to 17 were 20% in total.

<Example 1> Identification of Prevention, Treatment, Amelioration Effect of Hair-Loss, and Hair-Growth Stimulating Effect of *Centipeda minima* Extract Via Catagen Inhibition Animal Model Efficacy Test To proceed with the hair-growth efficacy test in the catagen inhibition animal model of *Centipeda minima* extract, male C57BL/6 mice (5 weeks of age) were purchased and subjected to acclimation for 1 week and selected animals weighing 16 to 21 g. In the case of an animal in which skin damage occurred during hair removal, or if the skin color was black, the growth period was already in progress, so it was inappropriate for this experiment and was excluded from the experiment.

The test group was divided into a normal group, a negative control group, a test substance-administered group, and a positive control groups 1 and 2. Each of the normal group and the negative control group had 1 mouse, the test substance-administered group had 3 mice, and the positive control group 1 had two mice, and the positive control group 2 had one mouse. Specifically, the normal group is a group not administered with a solvent or a test substance, the negative control group is a group receiving only a solvent, and the test substance group is a group administered with *Centipeda minima* extract of Preparation Example 3, the positive control group 1 is a Minoxidil-administrated group, the positive control group 2 is a group administered with *Litsea glutinosa* extract.

Tonic formulation (Preparation Example 1) of Preparation Example 3 was applied to the back skin for 7 days twice a day at 6 hour intervals at a dose of 100 µL. 0.1% 1 ml of dexamethasone (ferridex, green cross) as catagen-inducing substance was applied to the epilation site for 5 days. 5% 100 µl of dexamethasone was applied to the positive control groups 1 and 2.

During the experiment period, after administration of the test substance, hair-growth level was observed via photography and visual inspection. After the end of the experiment, animals were sacrificed and a pathology test for skin tissue was conducted.

Further, in order to quantify the results of hair-growth efficacy visual inspection, image analysis was performed on the entire epilation site (solvent or test substance, positive control substance application site) that is black (anagen) or a site where hair-growth begins. Image analysis was carried out with the image analysis program (ImagePro Plus 5.0, Cybernetics, USA). The result was quantified in %. The numerical data was converted to a numerical graph as produced using a graph production program (Prism 5.0, Graphpad, USA).

Example 1-1: Visual Inspection

Figure 3:
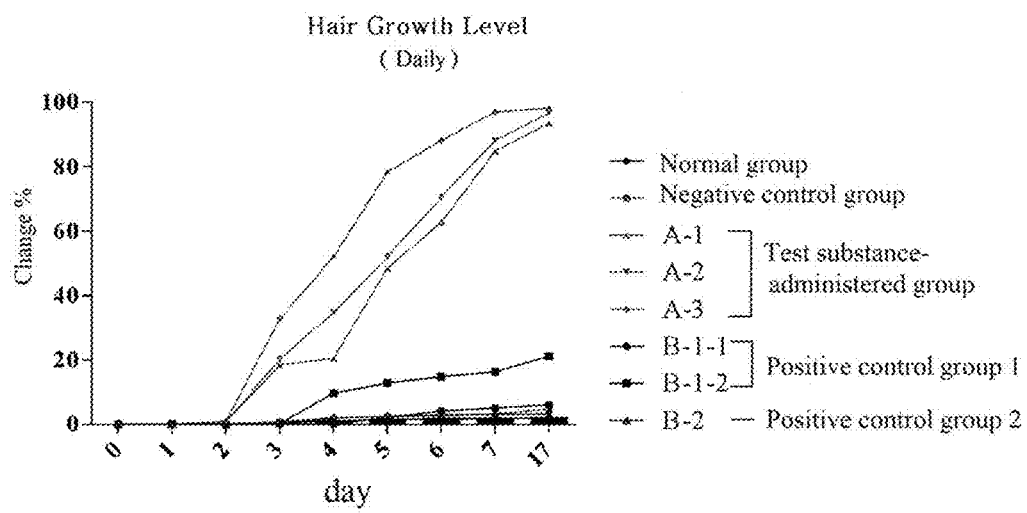
FIG. 3 is a graph quantifying the results of the hair-growth efficacy evaluation score through visual inspection in Example 1-1.
Figure 4:
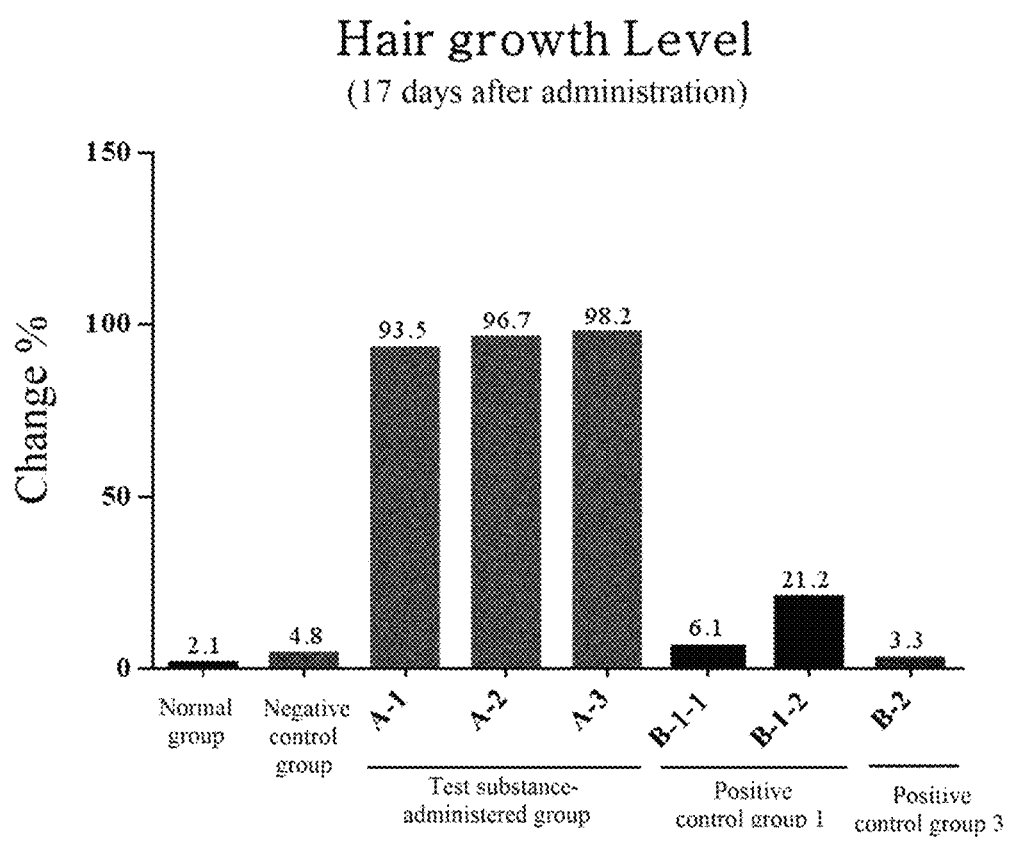
FIG. 4 is a graph quantifying the results of the hair-growth efficacy evaluation score through visual inspection after 7 days in Example 1-1.

Based on a result of visual inspection of the mouse skin, as shown in FIG. 1, FIG. 3 and FIG. 4, the test substance-administered group showed a significantly higher tendency (18.5%, 20.4%, 32.8%) to migrate to anagen on 3 days of administration, compared to other groups and could not be observed hair growth in positive control group 1 (0.1%, 0.3%) and positive control group 2 (0.4%). On 7 days of administration, the best hair-growth efficacy could be identified in the test substance-administered group (84.9%, 88.2%, 97.0%).

Further, as shown in FIG. 2, as a result of administering 0.1% of dexamethasone to maintain catagen, it may be visually identified that the hair-growth efficacy was excellent in the test substance-administered group (93.5%, 96.7%, 98.2%) finally on the Day 17 after administration. However, based on a result of more clearly identifying the hair follicle generation and hair-growth efficacy via the skin tissue pathology test, the positive control group 1 (6.1%, 21.2%) and positive control group 2 (3.3%) were unable to exhibit the excellent hair-growth efficacy like the test substance-administered group.

Therefore, it may be seen that the *Centipeda minima* extract according to the present disclosure may effectively act on the prevention, treatment and amelioration of hair-loss, and the promotion of hair-growth.

Example 1-2: Skin Tissue Pathology Test

The skin tissue pathology test was conducted by H&E staining using Hematoxylin and Eosin, which are generally used widely. A sample was collected from the skin tissue of the sacrificed animals and the generation of hair follicles and phenomena of hair-growth were identified through fixation, washing, clearing, paraffin infiltration, embedding, microtome cutting, staining and reading processes.

In this study, Anagen_Early (A/e) indicates the state in which hair has just begun to develop and Anagen_late (A/l) and Catagen_early (C/e) indicate that hair-growth is in full swing. Anagen_late and Catagen_early have histologically similar positions of the hair bulb. When considering morphological changes according to tissue sections, it is necessary to consider that it is often unclear to distinguish there between. Nevertheless, the hair follicles in the Anagen_late and Catagen_early stages are generally considered as similar stages of development, and the results are interpreted.

Figure 5:
FIG. 5 shows the observation of the tissues of the normal group, negative control group, test substance-administered group, positive control groups 1 and 2 in Example 1-2 as stained and observed with an optical microscope.

FIG. 5 shows the results of the analysis based on the above descriptions. As shown in FIG. 5, in the normal group and the negative control group, specific hair follicle generation and hair-growth efficacy could not be observed. Further, in the positive control group 1 and the positive control group 2, only minimal hair follicle generation and hair-growth efficacy degree could be observed. On the other hand, only the test substance-administered group to which *Centipeda minima* extract was administered was able to confirm the specifically excellent hair follicle generation and hair growth efficacy.

Therefore, it may be seen that the *Centipeda minima* extract according to the present disclosure may effectively act on the prevention, treatment and amelioration of hair-loss, and the promotion of hair-growth.

<Example 2> Identification of Prevention, Treatment and Amelioration Effects of Hair-Loss, and Hair-Growth Stimulating Effect of *Centipeda minima* Extract To proceed with the hair-growth efficacy test in the catagen inhibition animal model of *Centipeda minima* extract, male C57BL/6 mice (5 weeks of age) were purchased and subjected to acclimation for 1 week and selected animals weighing 20 to 24 g. In the case of an animal in which skin damage occurred during hair removal, or if the skin color was black, the growth period was already in progress, so it was inappropriate for this experiment and was excluded from the experiment.

The test group was divided into a normal group, a negative control group, a test substance-administered group, and a positive control groups 1 and 2. The normal group had three mice, the negative control group had 4 mice, the test substance-administered group had 4 mice, and the positive control group 1 (Tofacitinib) had four mice, and the positive control group 2 (Minoxidil) had four mice. Specifically, the normal group is a group not administered with a solvent or a test substance, the negative control group is a group receiving only a solvent, and the test substance group is a group administered with *Centipeda minima* extract of Preparation Examples 6, 8, 9 and 11 (30 or 100% ethanol, or 30 or 100% methanol), respectively. The positive control group 1 is a Tofacitinib-administrated group, and the positive control group 2 is a Minoxidil-administered group.

Each of the test substance preparation solutions of Preparation Example 2, 4, 5, and 7 were applied to the dorsal skin twice a day at intervals of 6 hours for 7 days at a dose of 100 μL. 0.1% 1 ml of dexamethasone (ferridex, green cross) as catagen-inducing substance was applied to the epilation site two days before the administration of the test substance, and the application thereof was repeated for 12 days, the end of the test. 5% 100 μl of dexamethasone was applied to the positive control groups 1 and 2.

During the experiment period, after administration of the test substance, hair-growth level was observed via photography and visual inspection. After the end of the experiment, animals were sacrificed and a pathology test for skin tissue was conducted.

Further, to quantify the results of hair-growth efficacy visual inspection, a black portion (anagen) or a region where hair-growth begins in the entire hair removal site (solvent or test substance, positive control substance application site) was visually observed. When anagen symptom was observed in less than 10% of an area to which each of the test substance, the negative control substance, and the positive control substance was applied in the entire hair removal region, score 1 was assigned. When anagen symptom was observed in 10% to 30% thereof, score 2 was assigned. When anagen symptom was observed in 30% to 50% thereof, score 3 was assigned. When anagen symptom was observed in 50% to 80% thereof, score 4 was assigned. When anagen symptom was observed in 80% to 100% thereof, score 5 was assigned. In this way, a numerical graph of the hair-growth efficacy evaluation score was produced.

Example 2-1: Visual Inspection

Figure 6:
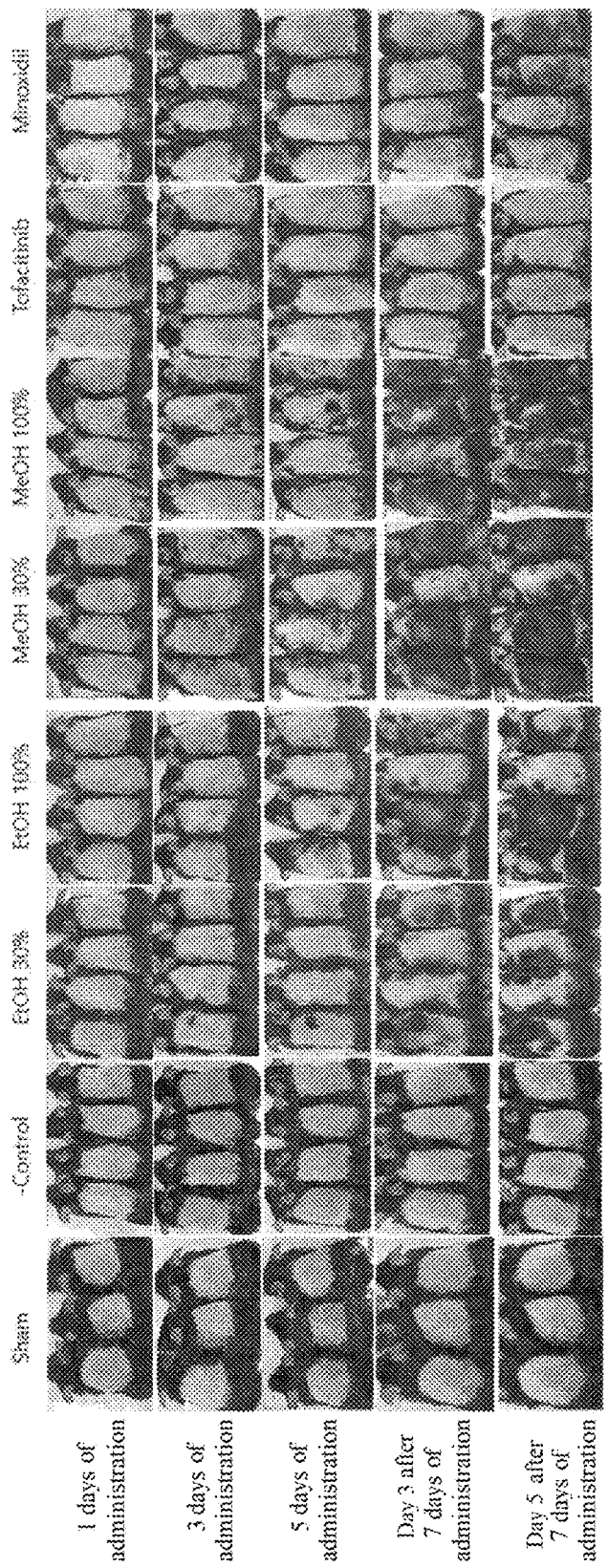
FIG. 6 shows a photograph of daily observation of a skin of each of the normal group, negative control group, test substance-administered group (*Centipeda minima* extract), positive control group 1 (Tofacitinib) and positive control group 2 (Minoxidil) in Example 2-1 until 12 days, and shows the result of the change in growth.

FIG. 6 shows the results of visual inspection of the mouse skin. As shown in FIG. 6, the test substance-administered group was found to have a significantly higher tendency to migrate to anagen on the Day 5 after 7 days of administration(+12 day), compared to the other groups.

Specifically, the hair-growth efficacy in each administered group on the Day 5 after 7 days of administration was shown in Table 1 below.

TABLE 1

| Test group | Hair-growth efficacy (%) |
|---|---|
| Tofacitinib | 25 |
| Minoxidil | 45 |
| EtOH 30% | 65 |
| EtOH 100% | 70 |
| MeOH 30% | 95 |
| MeOH 100% | 90 |

As may be seen above, excellent hair-growth efficacy could be identified in the *Centipeda minima* extract-administered group according to the present disclosure.

Figure 7:
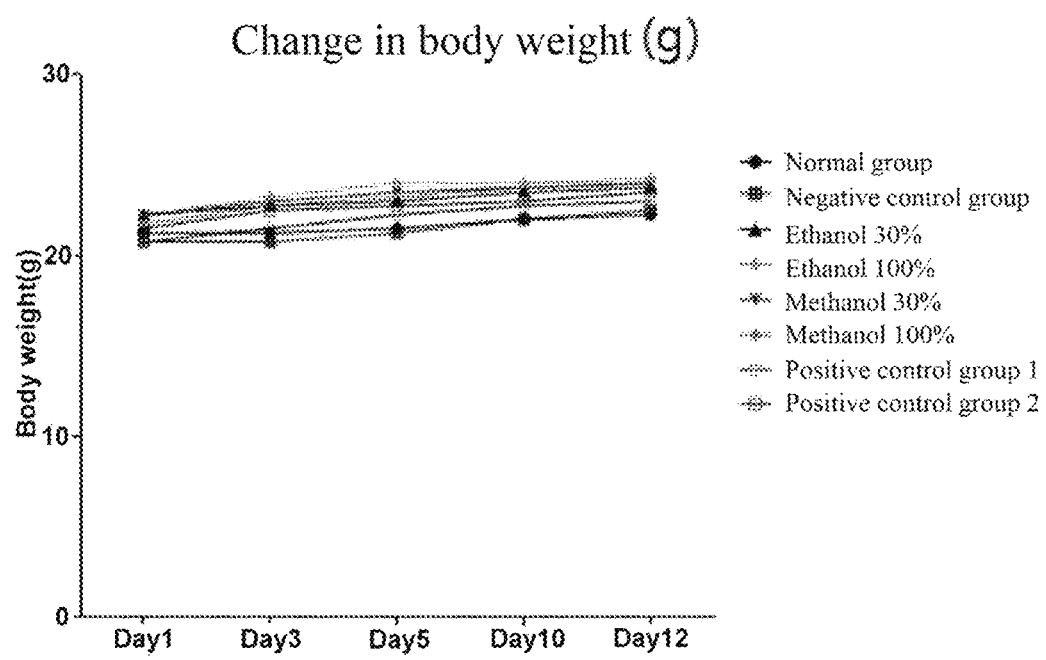
FIG. 7 shows the results of the change in the weight of the mouse during the test period of Example 2-1.
Figure 8:
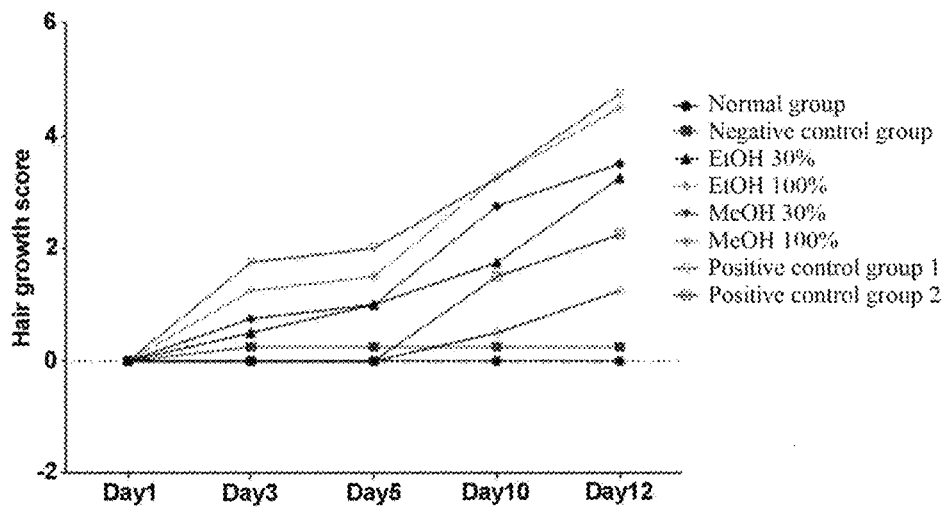
FIG. 8 shows the results obtained by quantifying the hair-growth efficacy evaluation score during the test period of Example 2-1. (A in FIG. 8: Daily hair-growth efficacy evaluation score, B in FIG. 8: Hair-growth efficacy evaluation score on Day 12.
Figure 8:
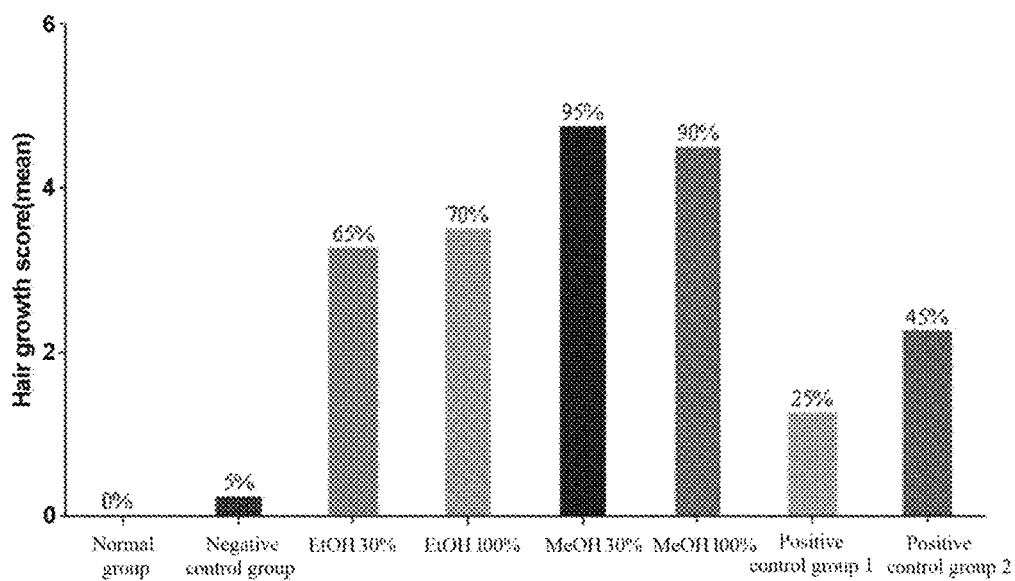

Further, the changes in body weight during the administration period and hair-growth efficacy evaluation scores during the administration period are shown in FIG. 7 and FIG. 8, respectively.

As shown in FIG. 7, it may be identified that there was no significant change in the weight of the mouse during the test period.

Further, as may be seen in FIG. 8, the *Centipeda minima* extract-administered group was able to exhibit a significant increase in the hair-growth efficacy during the test period. Specifically, as shown in A of FIG. 8, we may identify the excellent hair-growth efficacy in the test group administered with a *Centipeda minima* extract according to the present disclosure during the test period. As may be seen from B in FIG. 8, the test group administered with a *Centipeda minima* extract according to the present disclosure exhibits a much better effect than the positive control groups on the Day 12 of the final evaluation.

From the above results, it may be seen that the *Centipeda minima* extract according to the present disclosure may be effective in preventing, treating and ameliorating hair-loss and stimulating hair-growth.

Example 2-2: Skin Tissue Pathology Test

The skin tissue pathology test was conducted on day 12 by H&E staining using Hematoxylin and Eosin, which are widely used. A sample was collected from the skin tissue of the sacrificed animals and the generation of hair follicles and phenomena of hair-growth were identified through fixation, washing, clearing, paraffin infiltration, embedding, microtome cutting, staining and reading processes.

Figure 9:
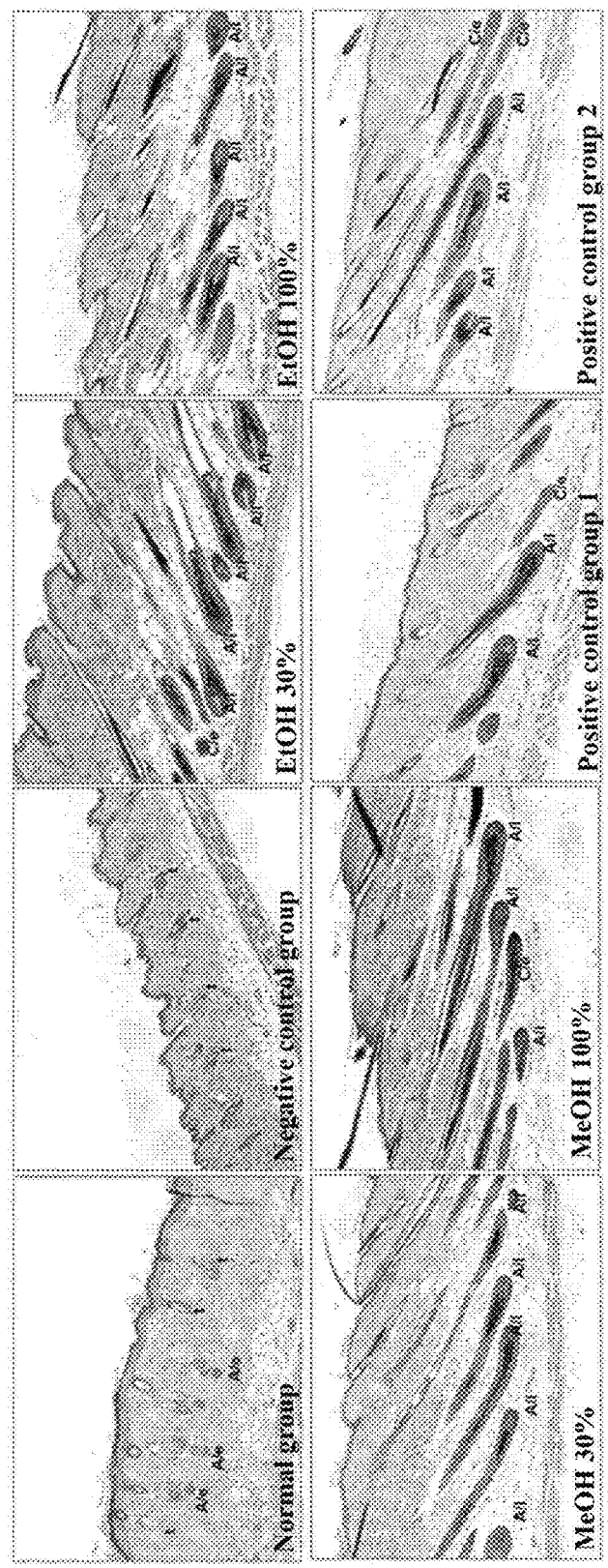
FIG. 9 shows the observation of the tissues of the normal group, negative control group, test substance-administered group (*Centipeda minima* extract), positive control group 1 and positive control group 2 in Example 2-2 as stained and observed with an optical microscope: Anagen_Early (A/e), Anagen_late (A/l), Catagen_early (C/e), telogen (t).

FIG. 9 shows the results.

As may be seen in FIG. 9, the formation of specific hair follicles and hair-growth efficacy could not be observed in the normal and negative control groups. Further, in the positive control group 1 and the positive control group 2, only minimal hair follicle generation and hair-growth efficacy degree could be observed.

However, specific hair follicle production and hair-growth efficacy could be identified only in the test substance-administered group administered with *Centipeda minima* extract.

<Example 3> Identification of Prevention, Treatment and Amelioration Effect of Hair-Loss, and Hair-Growth Stimulation Effect of *Centipeda minima* Fraction In the same manner as in Example 2, the hair-loss prevention, treatment, amelioration effects, and hair-growth stimulating effects using *Centipeda minima* fraction were identified.

Specifically, the normal group is a group not administered with a solvent or a test substance, and a negative control group is a group receiving only a solvent. The test substance group was a group administered with *Centipeda minima* fractions of Preparation Examples 12, 14, 15, and 17 (dichloromethane fraction of 30 or 100% ethanol, or dichloromethane fraction of 30 or 100% methanol), respectively.

The test substance preparation solutions Preparation Examples 8, 10, 11 and 13 were applied to the dorsal skin twice a day at intervals of 6 hours for 7 days at a dose of 100 μL, respectively. 0.1% 1 mL of dexamethasone (ferridex, green cross) as catagen inducing substance was applied to the epilation site two days before the administration of the test substance, and the application thereof was repeated for 12 days, the end of test. 5% 100 μl of dexamethasone was applied to positive control groups 1 and 2. The rest of the experimental method was the same as in Example 2.

Example 3-1: Visual Inspection

It may be specifically shown in Table 2 below that the test substance-administered group exhibited the significantly higher tendency to migrate to anagen on the Day 5 after 7 days of administration(+12 day), than those of the other groups. Table 2 shows hair-growth efficacy in each administered group on the Day 5 after 7 days of administration.

TABLE 2

| Test group | Hair-growth efficacy (%) |
|---|---|
| $CH_2Cl_2$ fraction of EtOH 30% extract | 40 |
| $CH_2Cl_2$ fraction of EtOH 100% extract | 50 |
| $CH_2Cl_2$ fraction of MeOH 30% extract | 45 |
| $CH_2Cl_2$ fraction of MeOH 100% extract | 65 |

As may be seen above, we may identify excellent hair-growth efficacy in the *Centipeda minima* fraction-administered group according to the present disclosure.

Figure 10:
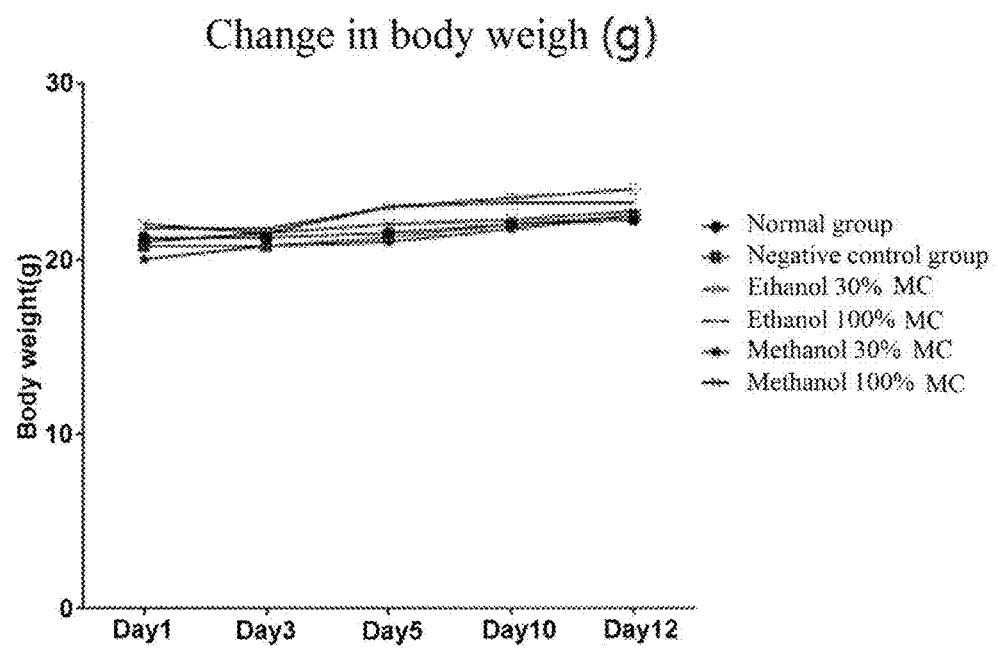
FIG. 10 is the result of the change in the weight of the mouse during the test period of Example 3-1.
Figure 11:
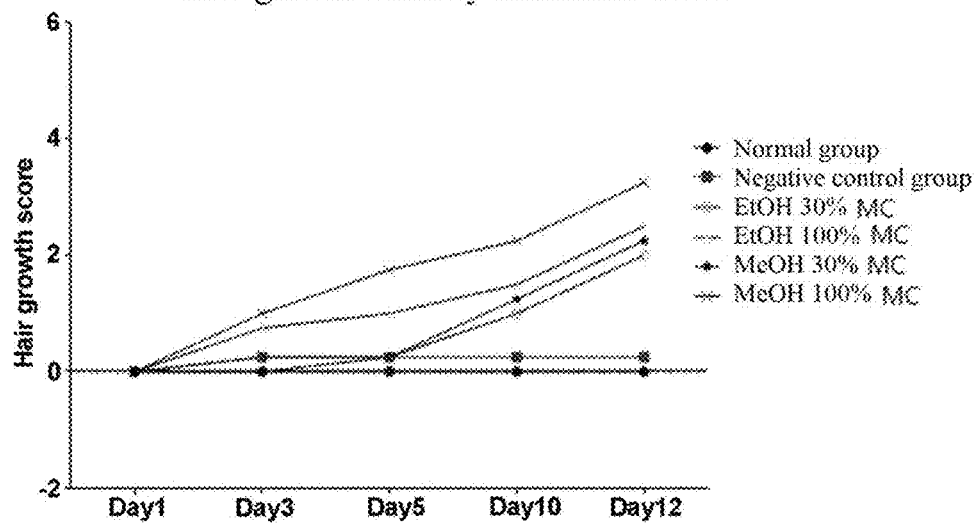
FIG. 11 shows the results obtained by quantifying the hair-growth efficacy evaluation score during the test period of Example 3-1 (A in FIG. 11: Daily hair-growth efficacy evaluation score, B in FIG. 11: Hair-growth efficacy evaluation score on Day 12.
Figure 11:
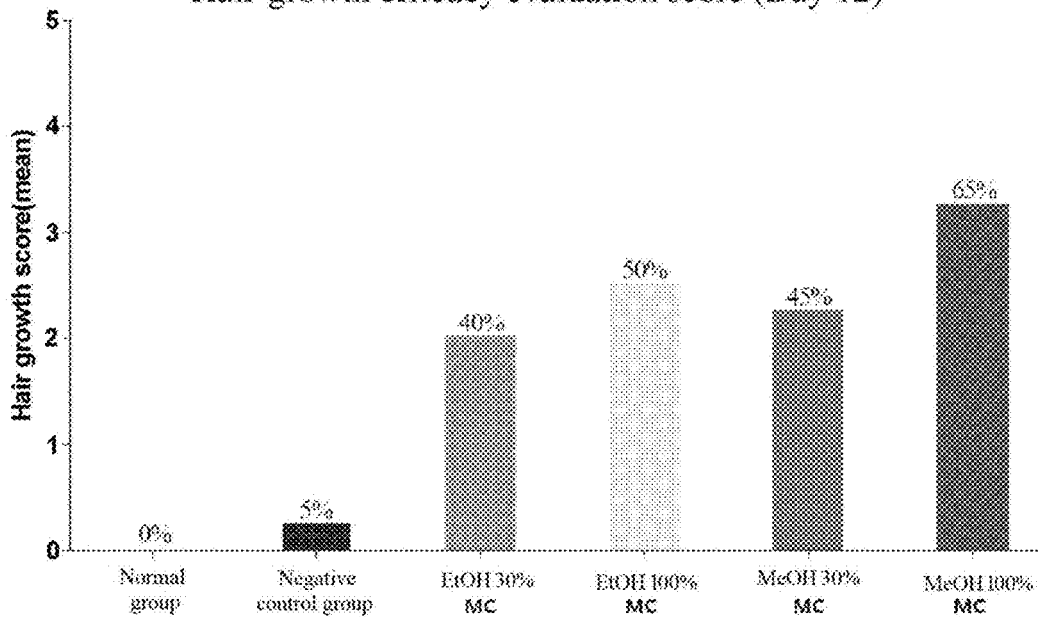

Further, the changes in the mouse body weight during the administration period and hair-growth efficacy evaluation scores during the administration period are shown in FIG. 10 and FIG. 11, respectively.

As may be seen in FIG. 10, we may identify that there was no significant change in the weight of the mouse during the test period.

Further, as may be seen in FIG. 11, the *Centipeda minima* fraction-administered group was able to exhibit a significant increase in hair-growth efficacy during the test period. Specifically, as shown in A in FIG. 11, the excellent hair-growth effects were identified in test groups administered with *Centipeda minima* fraction during the test period.

Further, as shown in B of FIG. 11, it was identified that hair-growth efficacy was remarkable on the Day 12 of the final evaluation.

From the above results, it may be seen that the *Centipeda minima* fraction according to the present disclosure may be effective in preventing, treating and ameliorating hair-loss and stimulating hair-growth.

Example 3-2: Skin Tissue Pathology Test

The skin tissue pathology test was conducted on day 12 by H&E staining using Hematoxylin and Eosin, which are widely used. A sample was collected from the skin tissue of the sacrificed animals and the generation of hair follicles and phenomena of hair-growth were identified through fixation, washing, clearing, paraffin infiltration, embedding, microtome cutting, staining and reading processes.

Figure 12:
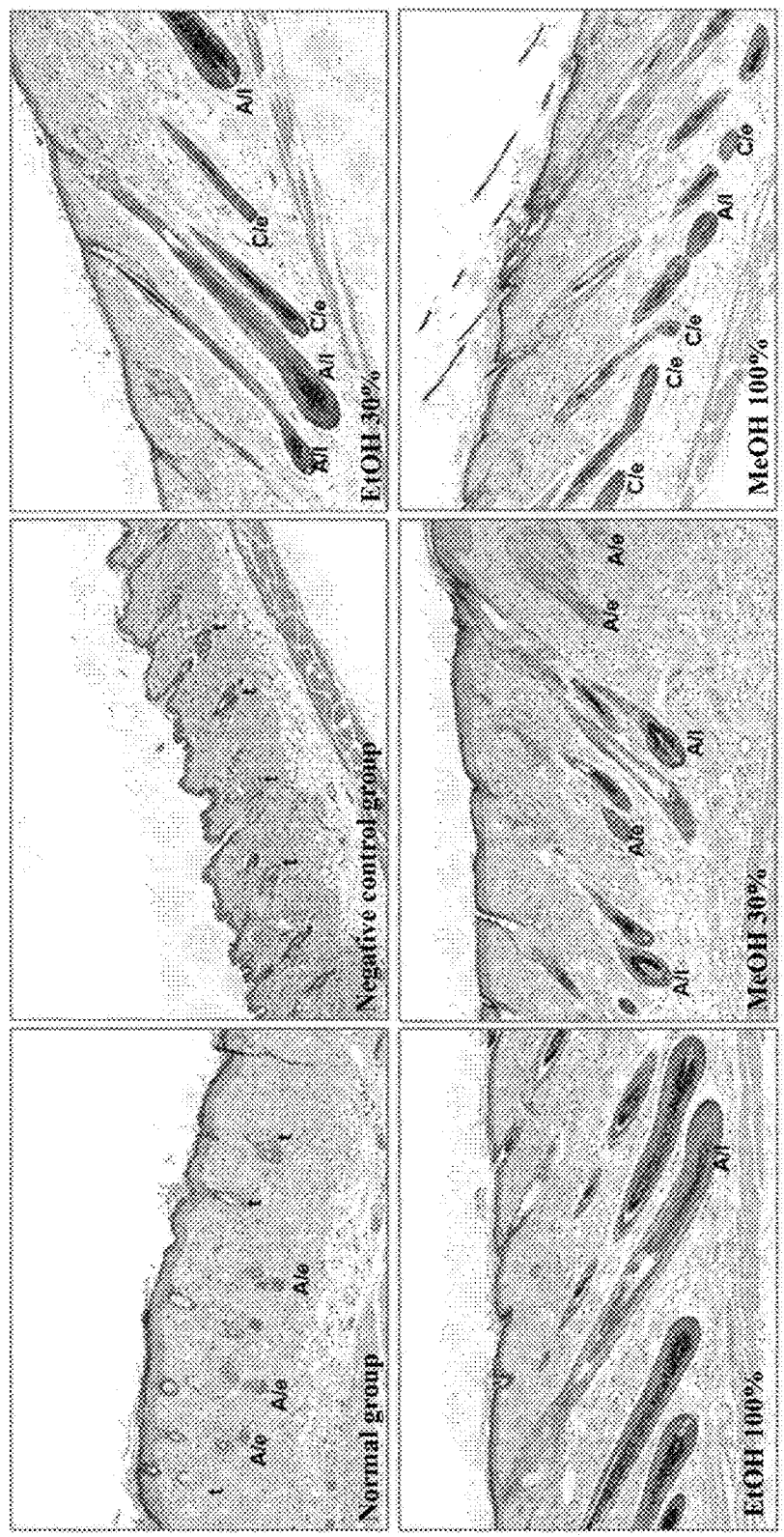
FIG. 12 shows that the tissues of the normal group, negative control group, and test substance-administered group (*Centipeda minima* fraction (MC: dichloromethane)) in Example 3-2 as stained and observed under an optical microscope: Anagen_Early (A/e), Anagen_late (A/l), Catagen_early (C/e), telogen (t).

The results are shown in FIG. 12.

As may be seen from FIG. 12, specific hair generation and hair-growth efficacy could not be observed in the normal and negative control groups. However, specific hair follicle production and hair-growth efficacy could be identified only in the test substance-administered group administered with *Centipeda minima* extract.

Based on the above results, it may be identified that the composition containing the *Centipeda minima* extract or the fraction thereof according to the present disclosure may promote hair generation and growth, and may quickly migrate the state of the hair follicle from the telogen to the anagen, thereby to achieve the excellent effect of stimulating hair-growth and its own health.

From the above description, a person skilled in the art to which the present disclosure belongs may understand that the present disclosure may be implemented in other specific forms without changing the technical idea or essential characteristics. In this regard, the examples as described above should be understood as illustrative in all respects and not restrictive. The scope of the present disclosure should be construed to include the meaning and scope of the patent claims as described later rather than the detailed description and all changes or modified forms derived from the equivalent concept included in the scope according to the present disclosure.

The invention claimed is:

1. A method of treating hair-loss comprising administering a therapeutically effective amount of a *Centipeda minima* extract or a fraction of the *Centipeda minima* extract to a subject in need thereof,
   wherein the *Centipeda minima* is a *Centipeda minima* 30 to 100% by weight methanol aqueous solution extract or a *Centipeda minima* 30 to 100% by weight ethanol aqueous solution extract, or
   wherein the fraction is a fraction of a *Centipeda minima* 30 to 100% methanol or ethanol extract obtained using dichloromethane as the fractioning solvent.

2. The method of claim 1, wherein the hair-loss includes at least one selected from a group consisting of denutrition-based alopecia, endocrine disorder-based alopecia, vascular disorder-based alopecia, alopecia premature, traction alopecia, alopecia areata, alopecia neurotica, pityriasis alopecia, Trichotillomania, alopecia maligna, female pattern alopecia, male pattern alopecia, androgenetic alopecia, telogen effluvium, tinea capitis, alopecia totalis, hypotrichosis, genetic hypotrichosis simplex, systemic drug for alopecia-based hair-loss, mechanical hair-loss, traumatic alopecia, pressure alopecia, anagen effluvium, alopecia syphilltica, alopecia seborrheica, symptomatic alopecia, alopecia cicatrisata, and alopecia congenita.

3. The method of claim 1, wherein the *Centipeda minima* extract or the fraction of the *Centipeda minima* extract is applied to the scalp or hair.

4. The method of claim 1, wherein the administering of *Centipeda minima* extract or the fraction of the *Centipeda minima* extract is transdermal administration.

5. The method of claim 1, wherein the *Centipeda minima* extract or the fraction of the *Centipeda minima* extract is formulated as an aerosol, ointment, liquid, lotion, patch, powder for application, oil, cream or gel.

\* \* \* \* \*

UNITED STATES PATENT AND TRADEMARK OFFICE
CERTIFICATE OF CORRECTION

PATENT NO. : 11,351,215 B2
APPLICATION NO. : 16/976061
DATED : June 7, 2022
INVENTOR(S) : Min Kyu Yang and Jwa Jin Kim It is certified that error appears in the above-identified patent and that said Letters Patent is hereby corrected as shown below:

In the Claims

Claim 1, Column 20, Line 9 reads:
"wherein the *Centipeda minima* is a *Centipeda minima* 30"
Whereas it should read:
"wherein the *Centipeda minima* extract is a *Centipeda minima* 30"

And

Claim 1, Column 20, Line 16 reads:
"dichloromethane as the fractioning solvent"
Whereas it should read:
"dichloromethane as the fractionating solvent"

Signed and Sealed this
Second Day of August, 2022

Katherine Kelly Vidal
*Director of the United States Patent and Trademark Office*